(12) United States Patent
Goodin et al.

(10) Patent No.: US 9,084,694 B2
(45) Date of Patent: Jul. 21, 2015

(54) COIL SHAFT

(75) Inventors: Richard Goodin, Blaine, MN (US);
Richard C. Gunderson, Maple Grove, MN (US); John R. Moberg, Elk River, MN (US); Katherine Prindle, Robbinsdale, MN (US); John Blix, Maple Grove, MN (US); Robert Burgmeier, Plymouth, MN (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 2007 days.

(21) Appl. No.: 11/223,370

(22) Filed: Sep. 9, 2005

(65) Prior Publication Data

US 2007/0060996 A1 Mar. 15, 2007

(51) Int. Cl.
| *A61F 2/06* | (2013.01) |
| *A61F 2/966* | (2013.01) |
| *A61F 2/95* | (2013.01) |
| *A61M 25/00* | (2006.01) |

(52) U.S. Cl.
CPC . *A61F 2/966* (2013.01); *A61F 2/95* (2013.01); *A61M 25/005* (2013.01)

(58) Field of Classification Search
CPC ........ A61F 2/95; A61F 2/966; A61M 25/005; A61M 25/0053
USPC ............. 623/1.22, 1.23, 1.11, 1.12, 1.3–1.31; 604/103.09, 526; 606/157, 200, 108
See application file for complete search history.

(56) References Cited

U.S. PATENT DOCUMENTS

| 4,795,458 | A | | 1/1989 | Regan |
| 5,147,317 | A | * | 9/1992 | Shank et al. ............. 604/164.13 |
| 5,203,772 | A | * | 4/1993 | Hammerslag et al. ........ 604/528 |
| 5,458,605 | A | | 10/1995 | Klemm |
| 5,573,520 | A | | 11/1996 | Schwartz et al. |
| 5,662,675 | A | | 9/1997 | Polanskyj Stockert et al. |
| 5,695,499 | A | | 12/1997 | Helgerson et al. |
| 5,743,876 | A | | 4/1998 | Swanson |
| 5,788,707 | A | | 8/1998 | Del Toro et al. |
| 6,022,343 | A | | 2/2000 | Johnson et al. |
| 6,322,534 | B1 | | 11/2001 | Shkolnik |
| 6,368,344 | B1 | | 4/2002 | Fitz |
| 6,520,934 | B1 | * | 2/2003 | Lee et al. .................. 604/103.1 |
| 6,679,909 | B2 | | 1/2004 | McIntosh et al. |
| 6,702,802 | B1 | * | 3/2004 | Hancock et al. ............. 604/524 |
| 6,709,425 | B2 | * | 3/2004 | Gambale et al. ............. 604/500 |
| 6,743,219 | B1 | | 6/2004 | Dwyer et al. |
| 7,731,742 | B2 | * | 6/2010 | Schlick et al. ............... 623/1.13 |
| 2002/0045929 | A1 | | 4/2002 | Diaz |
| 2003/0109886 | A1 | | 6/2003 | Keegan et al. |

(Continued)

FOREIGN PATENT DOCUMENTS

WO    WO 2005/110284    11/2005

OTHER PUBLICATIONS

Schetsky, L. McDonald, "Shape Memory Alloys", Encyclopedia of Chemical Technology (3rd Ed), John Wiley & Sons, 1982, vol. 20. pp. 726-736.

*Primary Examiner* — Elizabeth Houston
*Assistant Examiner* — Shaun L David
(74) *Attorney, Agent, or Firm* — Seager, Tufte & Wickhem, LLC

(57) ABSTRACT

Systems for delivering medical devices, as well as related methods are described.

9 Claims, 9 Drawing Sheets

(56) References Cited

U.S. PATENT DOCUMENTS

| | | |
|---|---|---|
| 2004/0002727 A1* | 1/2004 | Hwang et al. ............... 606/194 |
| 2004/0236346 A1 | 11/2004 | Parker |
| 2005/0038496 A1 | 2/2005 | Jones et al. |
| 2005/0113902 A1 | 5/2005 | Geiser et al. |
| 2005/0228479 A1 | 10/2005 | Pavcnik et al. |
| 2005/0288764 A1* | 12/2005 | Snow et al. ............... 623/1.11 |
| 2006/0015168 A1* | 1/2006 | Gunderson ............... 623/1.11 |
| 2006/0235502 A1* | 10/2006 | Belluche et al. ............. 623/1.11 |

* cited by examiner

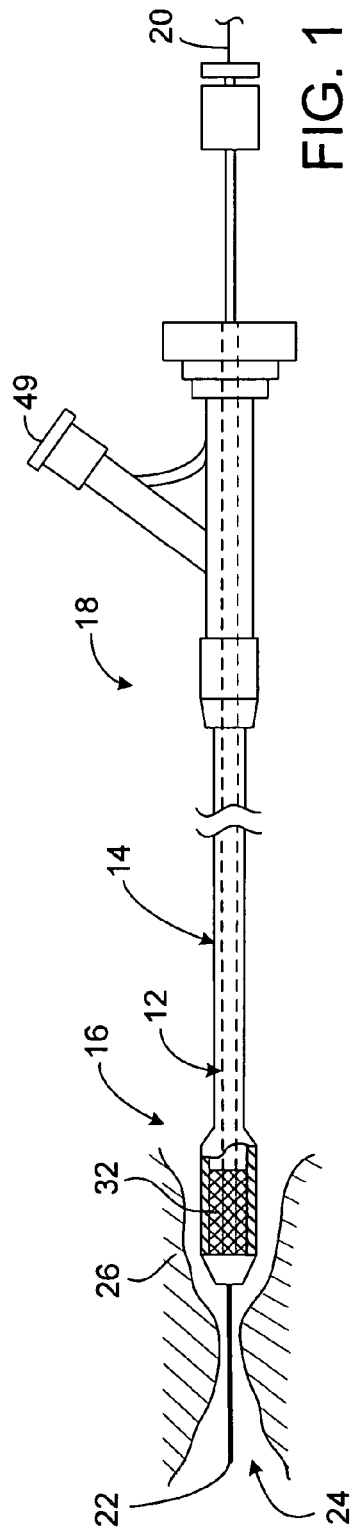
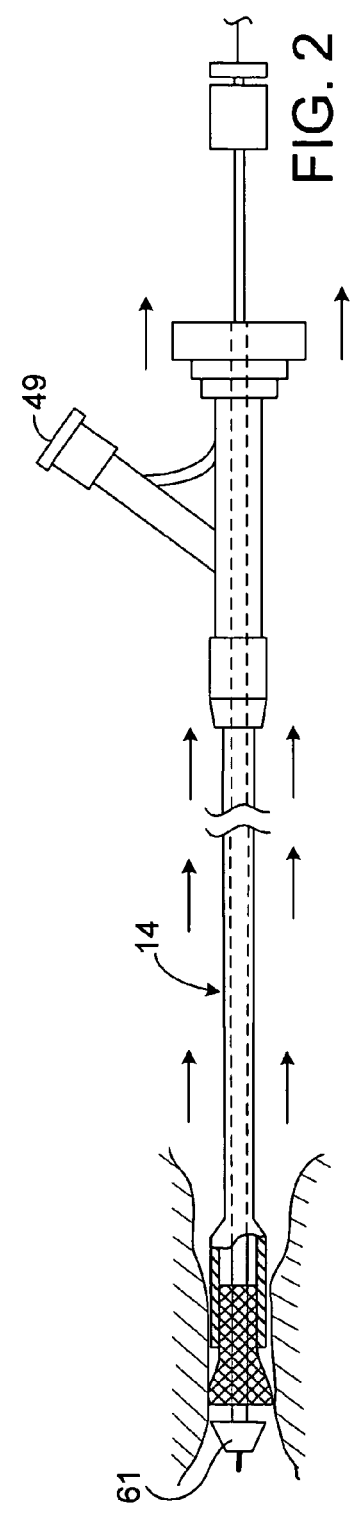
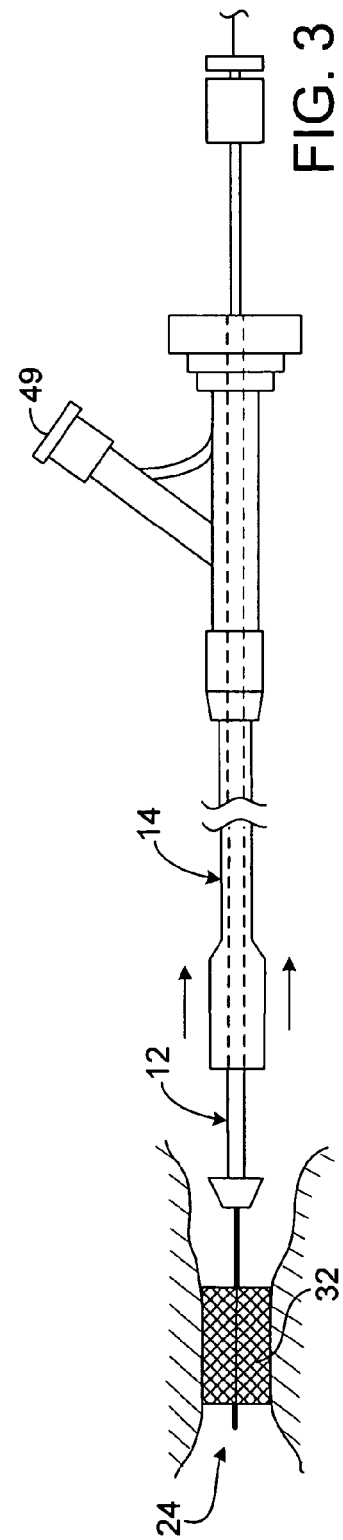

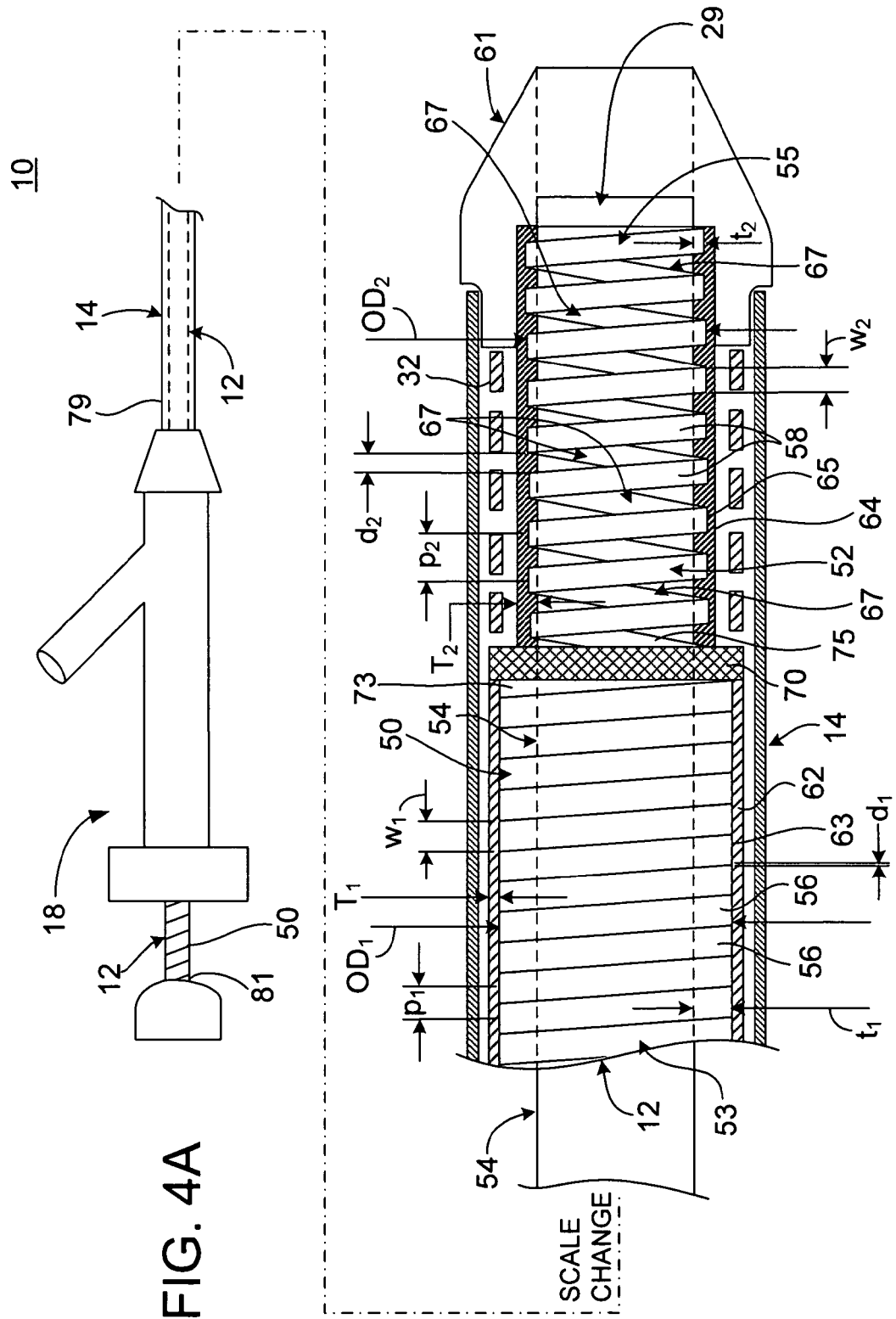

US 9,084,694 B2

COIL SHAFT

TECHNICAL FIELD

This invention relates to systems for delivering medical devices, as well as related systems and methods.

BACKGROUND

Systems are known for delivering medical devices, such as stents, into a body lumen. Often, such systems include a proximal portion that remains outside the body during use and a distal portion that is disposed within the body during use. The proximal portion typically includes a handle that is held by an operator of the system (e.g., a physician) during use, and the distal portion can include an outer member surrounding an inner member with a stent positioned therebetween. Generally, the operator of the system positions the distal portion within the lumen at a desired location (e.g., so that the stent is adjacent an occlusion). The operator can then retract the sheath to allow the stent to engage the occlusion/lumen wall. Thereafter, the operator removes the distal portion of the system from the lumen.

SUMMARY

In general, the invention relates to systems for delivering medical devices, as well as related methods. The systems can be used as, for example, implantable medical endoprosthesis delivery systems (e.g., stent delivery systems). The systems can be used, for example, to deploy a medical endoprosthesis (e.g., a stent, such as a self-expanding stent) at a desired location within a lumen of a subject (e.g., an artery of a human).

The systems generally include an outer member and at least one coil.

In some embodiments, the coil(s) include a plurality of spaced-apart windings. The systems can be configured so that a medical endoprosthesis can be disposed between the outer member and the plurality of windings. For example, a medical endoprosthesis (e.g., a stent) can be disposed so that it surrounds at least some of the windings.

In some embodiments, the systems include at least two coils with different outer diameters. At least a portion of one of the coils (e.g., the coil with the smaller outer diameter) may extend distally of the other coil. The system can be configured so that a medical endoprosthesis can be disposed between the outer member and at least a portion of one of the coils that extends distally of the other coil.

In some embodiments, the systems include first and second coils at least partially surrounded by the outer member. The second coil has an outer diameter larger than an outer diameter of the first coil and the system is configured so that an implantable medical endoprosthesis can be disposed between the outer member and at least a portion of at least one of the first and second coils.

In some embodiments, the systems include an outer member and an inner member at least partially surrounded by the outer member. The inner member includes first and second adjacent filars, where the first filar has a cross-section that is different from a cross-section of the second filar and the system is configured so that an implantable medical endoprosthesis can be disposed between the outer and inner members.

In some embodiments, the systems include an outer member, first and second coils at least partially surrounded by the outer member, a first tube surrounded by at least a portion of the first coil, and a second tube surrounded by at least a portion of the second coil. An outer diameter of the first tube is larger than an inner diameter of the second coil and the system is configured so that an implantable medical endoprosthesis can be disposed between the outer member and at least a portion of at least one of the first and second coils.

In some embodiments, a method for implanting an implantable medical endoprosthesis includes moving at least a portion of an implantable medical endoprosthesis delivery system along a lumen of a body, where the at least a portion of the implantable medical endoprosthesis delivery system includes an outer member, an implantable medical endoprosthesis at least partially surrounded by the outer member, and a plurality of spaced apart windings at least partially surrounded by the implantable medical endoprosthesis. The method also includes moving at least one of the outer member and the plurality of spaced apart windings with respect to the other to deploy the implantable medical endoprosthesis within the lumen.

The configuration of systems described herein can provide, for example, enhanced deployment accuracy. For example, in some embodiments, a coil provides resistance to longitudinal length changes (e.g., shortening) during use (e.g., when the outer member is moved to deploy a medical endoprosthesis such as a stent). In certain embodiments, a portion of a coil (e.g., a plurality of windings) surrounded by a medical endoprosthesis (e.g., a stent) resists buckling and/or kinking as the endoprosthesis is moved through a lumen.

Other features and advantages of the invention will be apparent from the description, drawings and claims.

DESCRIPTION OF DRAWINGS

FIGS. 1-3 are side views of an embodiment of an endoprosthesis delivery system during use.

FIG. 4a is an exploded, mixed view of an embodiment of an endoprosthesis delivery system.

FIG. 4b illustrates coils of an inner member of the delivery system of FIG. 4a.

FIG. 11b is a cross section of a filar of a coil of the inner member of FIG. 11a.

Like reference symbols in the various drawings indicate like elements.

DETAILED DESCRIPTION

Figure 4B:
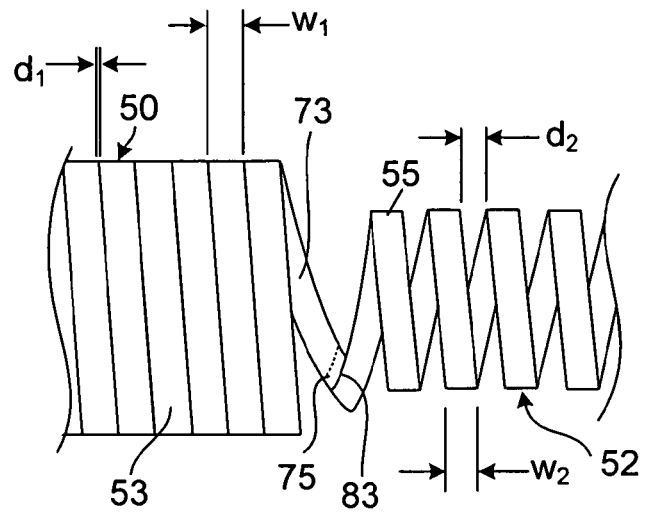

FIGS. 1-3 show an implantable medical endoprosthesis delivery system 10 that includes an inner member 12 (e.g., a catheter), an outer member 14 (e.g., a sheath) surrounding inner member 12, and a stent 32 positioned between inner member 12 and outer member 14. The delivery system 10 includes a distal end 16 dimensioned for insertion into a body lumen (e.g., an artery of a human) and a proximal end 18 that resides outside the body of a subject, and that contains at least one port 49 and lumens for manipulation by a physician. In an exemplary use of system 10, a guide wire 20 with a blunted end 22 is inserted into a body lumen 24 by making an incision in the femoral artery, and directing guide wire 20 to a constricted site 26 of lumen 24 (e.g., an artery constricted with plaque) using, for example, fluoroscopy as a position aid. After guide wire 20 has reached constricted site 26 of body lumen 24, inner member 12, stent 32 and outer member 14 are placed over the proximal end of guide wire 20. Inner member 12, stent 32 and outer member 14 are moved distally over guide wire 20 and positioned within lumen 24 so that stent 32 is adjacent constricted site 26 of lumen 24. Outer member 14 is moved proximally, allowing stent 32 to expand and engage constricted site 26. Outer member 14, inner member 12 and guide wire 20 are removed from body lumen 24, leaving stent 32 engaged with constricted site 26.

As shown in FIG. 4a, inner member 12 includes a proximal coil 50 and a distal coil 52, which both surround a tube 54. Proximal coil 50 is formed by a filar 53, which defines a plurality of windings 56. Distal coil 52 is formed by a filar 55, which defines a plurality of windings 58. Proximal coil 50 has an outer diameter OD1 and distal coil 52 has a smaller outer diameter OD2. Inner member 12 also includes a coating 62 that surrounds at least an outer surface 63 of proximal coil 50 and a coating 64 that surrounds at least an outer surface 65 of distal coil 52.

In general, filar 53 and proximal coil 50 can have properties (e.g., a width, pitch, thickness, diameter, and composition) that provide desired deliverability properties (e.g., flexibility, resistance to kinking, and/or resistance to longitudinal compression).

Filar 53 of proximal coil 50 has a width w1. For example, in some embodiments, width w1 is at least about 175 microns (e.g., at least about 225 microns, at least about 275 microns, at least about 325 microns). In some embodiments, width w1 is at most about 550 microns (e.g., at most about 425 microns, at most about 350 microns, at most about 300 microns). In an exemplary embodiment, width w1 is about 380 microns.

Consecutive windings 56 of proximal coil 50 have a pitch p1. In general, pitch p1 can be different from or of about the same dimension as width w1. For example, in certain embodiments, pitch p1 is no more than about 7.5% greater than w1 (e.g., no more than about 5% greater, no more than about 2.5% greater, no more than about 1% greater) when inner member 12 is in a relaxed (e.g., uncompressed), generally straight configuration.

In general, windings 56 of proximal coil 50 are configured so that the proximal coil resists length changes (e.g., shortening) when compressed (e.g., during proximal movement of outer member 14 to deploy stent 32). In certain embodiments, an average distance d1 between adjacent windings 56 is about zero so that coil 50 has little or no room to shorten when compressed. For example, proximal coil 50 can be formed with adjacent windings under compression (e.g., coil 50 can be formed as a close wound coil with pre-load or as a tight wound coil). In such embodiments, adjacent windings 56 generally contact one another and pitch p1 is about equal to width w1 when inner member 12 is in a relaxed, generally straight configuration. For example, proximal coil 50 can be formed such that the windings are under compression with respect to one another. In some embodiments, average distance d1 is at most about 50 microns (e.g., at most about 20 microns, at most about 5 microns, at most about 2 microns) when inner member 12 is in a relaxed, generally straight configuration.

Filar 53 of proximal coil 50 has a thickness t1. In some embodiments, thickness t1 is at least about 45 microns (e.g., at least about 60 mm, at least about 80 mm, at least about 90 microns). In some embodiments, thickness t1 is at most about 150 microns (e.g., at most about 110 microns, at most about 90 microns, at most about 70 microns). In an exemplary embodiment, thickness t1 is about 100 microns.

In some embodiments, OD1 of proximal coil 50 is at least about 1.0 mm (e.g., at least about 1.25 mm, at least about 1.35 mm, at least about 1.45 mm). In some embodiments, OD1 of proximal coil 50 is at most about 3.0 mm (e.g., at most about 1.5 mm, at most about 1.4 mm, at most about 1.3 mm). For example, in some embodiments, OD1 is between about 1.25 and about 1.35 mm.

In general, filar 55 of proximal coil 52 can have properties (e.g., a width, pitch, thickness, diameter, and composition) that provide desired deliverability properties (e.g., flexibility, resistance to kinking, and/or resistance to longitudinal compression).

Filar 55 of distal coil 52 has a width w2. In some embodiments, width w2 is at least about 50 microns (e.g., at least about 75 microns, at least about 150 microns, at least about 225 microns). In some embodiments, width w2 is at most about 300 microns (e.g., at most about 225 microns, at most about 150 microns). In an exemplary embodiment, width w2 is about 200 microns.

Adjacent windings 58 of distal coil 52 define a pitch p2. In general, pitch p2 is as large as or larger than width w2 of filar 55 of distal coil 52. For example, in certain embodiments, pitch p2 is at least about 20% (e.g., at least about 30%, at least about 50%, at least about 75%, at least about 100%) larger than w2 when inner member 12 is in a relaxed, generally straight configuration. In some embodiments, pitch p2 is no larger than about 200% (e.g., no larger than about 125%, no larger than about 65%, no larger than about 45%) of w2 when inner member 12 is in a relaxed generally straight configuration.

Adjacent windings 58 of distal coil 52 are spaced-apart from one another by a distance d2 and define a gap 67 therebetween. In some embodiments, distance d2 is greater than distance d1 between adjacent windings 56 of proximal coil 50 when inner member 12 is in a relaxed, generally straight configuration. For example, in some embodiments, the ratio of d2 to d1 is at least about 2 (e.g., at least about 10, at least about 25, at least about 50) when inner member 12 is in a relaxed, generally straight configuration. In some embodiments, distance d2 is at least about 20% (e.g., at least about 30%, at least about 50%, at least about 75%, at least about 100%) of w2 when inner member 12 is in a relaxed generally straight configuration.

Filar 55 of distal coil 52 has a thickness t2. In some embodiments, thickness t2 is at least about 30 microns (e.g., at least about 40 microns, at least about 50 microns, at least about 75 microns). In some embodiments, thickness t2 is at most about 150 microns (e.g., at most about 100 microns, at most about 80 microns, at most about 55 microns). In general, t2 of filar 55 is less than t1 of filar 53 of proximal coil 50. In an exemplary embodiment, thickness t2 is about 50 microns.

In some embodiments, OD2 of distal coil 52 is at least about 0.9 mm (e.g., at least about 1.05 mm, at least about 1.2 mm). In some embodiments, OD2 of distal coil 52 is at most about 2.5 mm (e.g., at most about 1.3 mm, at most about 1.2 mm). In some embodiments, OD1 of proximal coil 50 is at least about 2.5% larger (e.g., at least about 5% larger, at least about 7.5% larger) than OD2 of distal coil 52. In an exemplary embodiment, OD2 is about 1.27 mm.

Referring to FIG. 4b, proximal coil 50 and distal coil 52 are, in general, relatively secured, such as to limit or prevent longitudinal movement of one coil with respect to the other. Typically, a distal end 73 of filar 53 of proximal coil 50 is secured at a joint 83 to a proximal end 75 of filar 55 of distal coil 52. In some embodiments, ends 73 and 75 are secured by a metallic bond, such as by soldering, brazing, or welding. Alternatively or in addition, ends 73 and 75 can by secured by a polymeric material (e.g., distal end 73 and proximal end 75 can be set in a polymer, such as an adhesive or a thermally flowed polymer).

As seen in FIG. 4a, proximal coil 50 extends proximally of outer member 14 when the outer member surrounds stent 32 (e.g., before outer member 14 has been moved proximally to deploy stent 32). Proximal coil 50 extends to a proximal end 81 of inner member 12. The proximal end 81 is disposed proximal to a proximal end 79 of outer member 14.

Tube 54 extends along at least a portion (e.g., most or all) of inner member 12. An inner lumen 29 of tube 54 defines a guidewire lumen.

Proximal coil 50 surrounds a proximal portion of tube 54 and distal coil 52 surrounds a distal portion of tube 54. The inner diameter of proximal coil 50 is larger than the outer diameter of tube 54. The inner diameter of distal coil 52 is about the same as the outer diameter of tube 54. In general, at least some windings 58 of distal coil 52 are secured (e.g., adhesively and/or thermally) with respect to tube 54. For example, distal coil 52 can be formed by winding filar 55 about tube 54, which is supported by a mandrel. The assembly is optionally heated so as to at least partially flow tube 54 about at least a portion of filar 55.

Tube 54 is typically made of a polymeric material. Examples of polymeric materials include polyether-block co-polyamide polymers (e.g., PEBAX®), copolyester elastomers (e.g., Arnitel® copolyester elastomers), thermoplastic polyester elastomers (e.g., Hytrel®), thermoplastic polyurethane elastomers (e.g., Pellethane™), polyolefins (e.g., Marlex® polyethylene, Marlex® polypropylene), HDPEs, low-density polyethylenes (LDPEs), polyamides (e.g., Vestamid®), fluoropolymers (e.g., PTFE), and combinations of these materials.

In some embodiments, tube 54 is at least about 25 microns (e.g., at least about 35 microns, at least about 50 microns) thick. In certain embodiments, tube 54 is no thicker than about 40 microns (e.g., no thicker than about 60 microns, no thicker than about 75 microns).

Coating 64 surrounds at least some (e.g., most or all) of distal coil 52 (e.g., its outer surface) and at least partially fills gaps 67 between its adjacent windings 58. In general, coating 64 secures at least some windings 58 of distal coil 52 with respect to tube 54 (e.g., coating 64 may bind to both distal coil 52 and to tube 54). In some embodiments, coating 64 is integral with tube 54. Examples of materials from which coating 64 can be made include polymeric materials such as polyether-block co-polyamide polymers (e.g., PEBAX®), nylons, and thermoplastic polyester elastomers (e.g., Hytrel®). Additional examples of polymeric materials include heat shrink materials such as cross-linked polyethylene, polyester (e.g., PET) heat shrink, fluorinated ethylene (FEP) heat shrink, and polytetrafluoroethylene (PTFE) heat shrink. In some embodiments, coating 64 includes an additive (e.g., a fluoropolymer, a silicone, an ultrahigh molecular weight polyethylene, an oil, or blends thereof) to assist in the movement of outer member 14 with respect to inner member 12.

Coating 62 of proximal coil 50 is typically made of a polymeric material. Examples of suitable materials include those noted above with respect to coating 64.

In some embodiments, coatings 62, 64 are formed of different materials. For example, coating 62 can be formed of a material having a higher durometer than the material from which coating 64 is formed. In certain embodiments, coating 64 is formed of a material (e.g., a polyether-block co-polyamide polymer (e.g., PEBAX®)) having a durometer of about 50 D or less (e.g., about 40 D or less about 35 D or less) and coating 62 is formed of a material (e.g., a polyamide or polyester) having a durometer of about 50 D or more (e.g., about 55 D or more, about 60 D or more).

Coating 62 and/or coating 64 can have different properties along their lengths. For example, coating 62 and/or coating 64 can have a higher durometer proximally than distally.

Without being bound by theory, it is believed that coatings 62 and 64 can respectively help maintain a position of windings 56 and 58 (e.g., the coatings can reduce or prevent undercutting of the windings (e.g., one winding sliding beneath an adjacent winding) as inner member 12 is moved within lumen 24 and/or when outer member 14 is moved proximally to deploy stent 32) while maintaining flexibility of proximal and distal coils 50, 52.

Coating 62 and/or coating 64 can include a radiopaque material (e.g., a ceramic, bismuth sulfate) to assist in positioning system 10 within lumen 24. In certain embodiments, a radiopaque material within one or both of coatings 62, 64 is disposed to indicate a position of a proximal portion of stent 32. For example, radiopaque material can be aligned with or positioned generally adjacent to a distal end 73 of proximal coil 50 and/or proximal end 75 of distal coil 52.

In some embodiments, coating 62 and/or coating 64 include a material that enhances a lubricity and/or durability of an outer surface of inner member 12. Exemplary materials include particles formed of, for example, ceramics and/or silica. The particles can be embedded within or blended within the coating.

In some embodiments, coatings 62, 64 have a respective thickness T1, T2 of at least about 15 microns (e.g., at least about 20 microns, at least about 40 microns). In some embodiments, one or both thicknesses T1, T2 are no more than about 350 microns (e.g., no more than about 150 microns, no more than about 100 microns). In some embodiments, one or both thicknesses T1, T2 are from about 25 microns to about 250 microns (e.g., from about 50 microns to about 200 microns, about 150 microns).

Coatings 62 and 64 can be formed as desired. For example, the coatings can be formed by dip coating, thermally reflowing a polymer applied to the coil, or spray coating.

Filars 53, 55 of proximal and distal coils 50, 52 can be formed of, for example, a metal, an alloy, or a polymeric material. Examples of metals include platinum and gold. Examples of alloys include gold-containing alloys, platinum-containing alloys, stainless steel and shape memory alloys. Examples of shape memory alloys include nitinol, silver-cadmium (Ag—Cd), gold-cadmium (Au—Cd), gold-copper-zinc (Au—Cu—Zn), copper-aluminum-nickel (Cu—Al—Ni), copper-gold-zinc (Cu—Au—Zn), copper-zinc/(Cu—Zn), copper-zinc-aluminum (Cu—Zn—Al), copper-zinc-tin (Cu—Zn—Sn), copper-zinc-xenon (Cu—Zn—Xe), iron beryllium (Fe3Be), iron platinum (Fe3Pt), indium-thallium (In—Tl), iron-manganese (Fe—Mn), nickel-titanium-vanadium (Ni—Ti—V), iron-nickel-titanium-cobalt (Fe—Ni—

Ti—Co) and copper-tin (Cu—Sn). For yet additional shape memory alloys, see, for example, Schetsky, L. McDonald, "Shape Memory Alloys", Encyclopedia of Chemical Technology (3rd ed.), John Wiley & Sons, 1982, vol. 20. pp. 726-736. Examples of polymeric materials include nylons, aramids (e.g., Kevlar), thermoplastic polyester elastomers (e.g., Hytrel®), copolyester elastomers (e.g., Arnitel® copolyester elastomers), polyether-block co-polyamide polymers (e.g., PEBAX®) and high-density polyethylene (HD-PEs).

Typically, outer member 14 includes a polymeric material. Examples of polymeric materials include those noted above with respect to tube 54. In some embodiments, outer member 14 includes an additive (e.g., a fluoropolymer, a silicone, an ultrahigh molecular weight polyethylene, an oil, or blends thereof) to assist in the movement of outer member 14 with respect to inner member 12 and stent 32. Outer member 14 can include a reinforcing layer (e.g., a braid and/or coil) along at least a portion (e.g., most or all) of its length to reduce elongation of the outer member during deployment of stent 32.

FIG. 4a shows that system 10 further includes a bumper 70 and a distal tip 61 that are integral with inner member 12. Bumper 70 can reduce the possibility of stent 32 moving proximally as outer member 14 is moved proximally, and tip 61 can assist in positioning of system 10 within body lumen 24 (e.g., as system 10 is moved distally over guide wire 20 within body lumen 24). In some embodiments, bumper 70 is formed of a polymeric material, such as a polyether-block co-polyamide polymer (e.g., PEBAX®) or a thermoplastic polyurethane elastomer (e.g., Pellethane™). In certain embodiments, bumper 70 is made of a metal or an alloy, such as, for example, stainless steel, Nitinol and/or platinum. Tip 61 is typically formed of a relatively soft polymeric material.

Figure 5A:
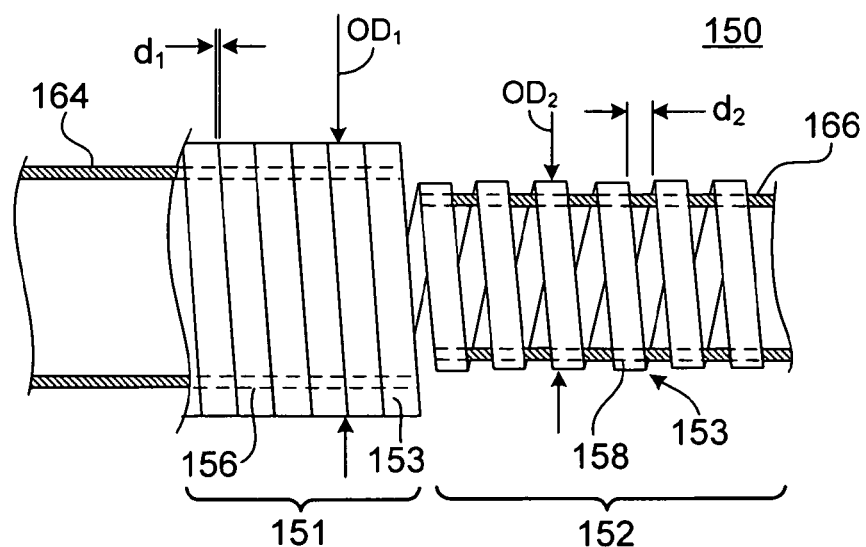
FIG. 5a is a partial side view of an embodiment of a coil of an inner member of an endoprosthesis delivery system.

While inner member 12 has been described as having proximal and distal coils defined by different filars, other configurations can be used. For example, referring to FIG. 5a, a coil 150 of an inner member includes a proximal portion 151 and a distal portion 152 defined by a common filar 153, which is continuous between the proximal and distal portions. Proximal portion 151 of coil 150 surrounds a tube 164 and distal portion 152 surrounds a tube 166. The outer diameter of tube 164 is about the same as the inner diameter of proximal portion 151 and the outer diameter of tube 166 is about the same as the inner diameter of distal portion 152. The outer diameter of tube 164 is generally larger than the inner diameter of distal portion 152.

Other than the continuity of filar 153 between proximal and distal portions 151, 152, other properties (e.g., outer diameter(s), filar width(s), filar thickness(es), distance(s) between adjacent windings, pitch(es), filar material, filar cross sectional shape(s)) of coil 150 may be similar to or the same as those of coils 50 and 52 described above. For example, within proximal portion 151, adjacent windings 156 are disposed within distance d1 (which may be about zero) of one another and within distal portion 152, adjacent windings 158 are spaced-apart by distance d2. The outer diameter of proximal portion 151 is OD1 and the outer diameter of distal portion 152 is the smaller OD2.

An inner member including coil 150 can be formed as desired. Typically, the method includes using a mandrel with a first portion having an outer diameter of about the same dimension as the inner diameter of tube 164 and a second portion with a smaller outer diameter of about the same dimension as the inner diameter of tube 166. Tube 164 is positioned over the first portion of the mandrel and tube 166 is positioned over the second portion of the mandrel. Filar 153 is wound with distance d2 between adjacent windings about the outer surface of tube 166 to form distal portion 152 and with distance d1 between adjacent windings about the outer surface of tube 164 to form proximal portion 151. An outer coating or layer (e.g., a heat shrink material) is disposed about proximal portion 151 and/or distal portion 152. The assembly is heated to reflow the outer coating or layer and secure the respective windings of the proximal and distal coil portions with respect to tubes 164 and 166. In some embodiments, the assembly includes joining (e.g., by heating) a distal end of tube 164 with a proximal end of tube 166. Proximal portion 151 can be compressed during at least a portion of the process to minimize distance d1 between its adjacent windings.

Figure 5B:
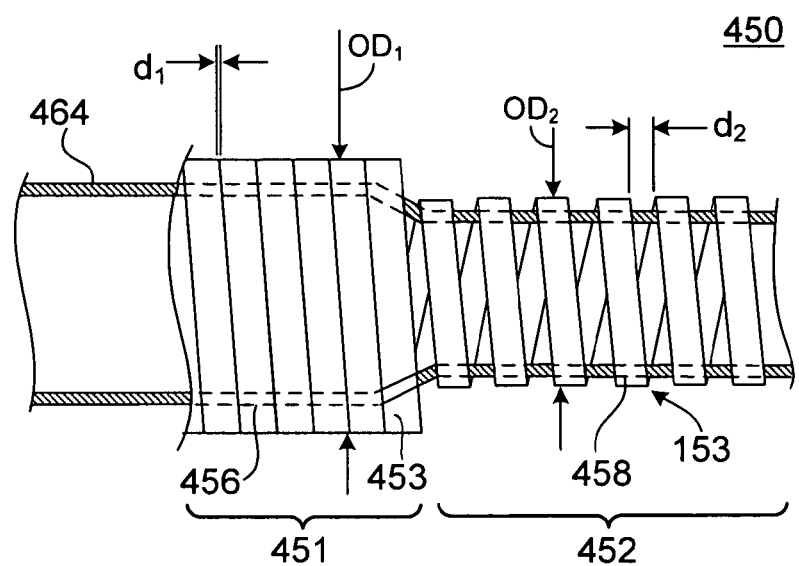
FIG. 5b is a partial side view of an embodiment of a coil of an inner member of an endoprosthesis delivery system.

While proximal and distal portions 151, 152 of coil 150 have been described as surrounding different tubes, other configurations can be used. For example, referring to FIG. 5b, a coil 450 of an inner member includes a proximal portion 451 and a distal portion 452. Proximal and distal portions 451, 452 both surround a tube 464, which is continuous between the proximal and distal portions. Within proximal portion 451, the outer diameter of tube 464 is generally about the same as the inner diameter of the proximal portion. Within distal portion 452, the outer diameter of tube 464 is generally about the same as the inner diameter of the distal portion. At least portions (e.g., most or all) of proximal portion 451 and/or distal portion 452 can be secured with respect to tube 464.

Other than continuity of tube 464, other properties (e.g., outer diameter(s), filar width(s), filar thickness(es), distance(s) between adjacent windings, pitch(es), filar material, filar cross sectional shape(s)) of coil 450 may be the same as for other coils described herein. For example, coil 450 is defined by a filar 453, which is continuous between the proximal and distal portions 451, 452.

Coil 450 can be formed as desired. Typically, the method includes positioning tube 464 about a mandrel with a first portion having an outer diameter about the same as the inner diameter of tube 464 within proximal portion 451 and a second portion having an outer diameter about the same as the smaller inner diameter of tube 464 within distal portion 452. Prior to assembly, the outer diameter of tube 464 is generally about the same as the inner diameter of distal coil portion 452. Tube 464 is positioned over the first and second portions of the mandrel. In general, tube 464 is stretched (e.g., with heating) over the first larger diameter portion of the mandrel. The proximal and distal coil portions are wound about the tube. The method can then proceed as described above.

Figure 6:
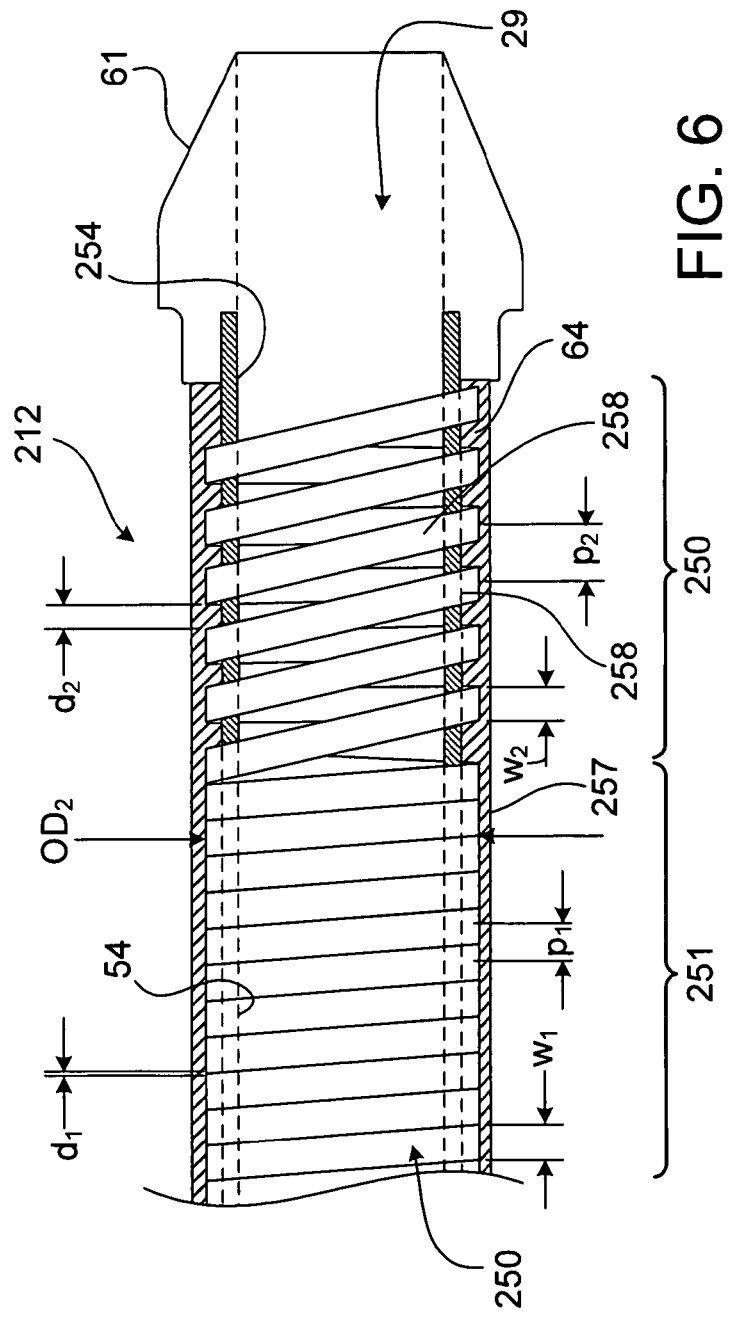
FIG. 6 is a partial side view of an embodiment of an inner member of an endoprosthesis delivery system.

While inner members having proximal and distal coils of different outer diameters have been described, coils of an inner member can have other configurations. For example, referring to FIG. 6, an inner member 212 includes a coil 250 having a proximal portion 251 and a distal portion 252 having the same outer diameter OD2. Inner member 212 is configured so that a medical endoprosthesis (e.g., a stent) can be disposed to surround the distal portion 252. Outer member 14 surrounds at least some (e.g., most or all) of the endoprosthesis. Coil 250 at least partially surrounds and can be secured with respect to a tube 254.

Other than the outer diameters of proximal and distal portions 251, 252, other properties (e.g., outer diameter(s), filar width(s), filar thickness(es), distance(s) between adjacent windings, pitch(es), filar material, filar cross sectional shape(s)) of coil 250 may be the same as for other coils described herein. A bumper, not shown, may be secured about inner member 212 to prevent proximal movement of the endoprosthesis during deployment. Typically, the bumper is disposed at a transition portion 257 between proximal and distal coil portions 251, 252. Other properties of inner member 212 may be the same as described above for inner member 12.

An inner member with coil 250 can be formed as desired. Typically, the method includes positioning tube 254 over a mandrel. Coil 250 is wound around tube 254. A coating (e.g., coating 64 and/or coating 62) is applied over coil 250. The assembly can be heated as described above.

Figure 7:
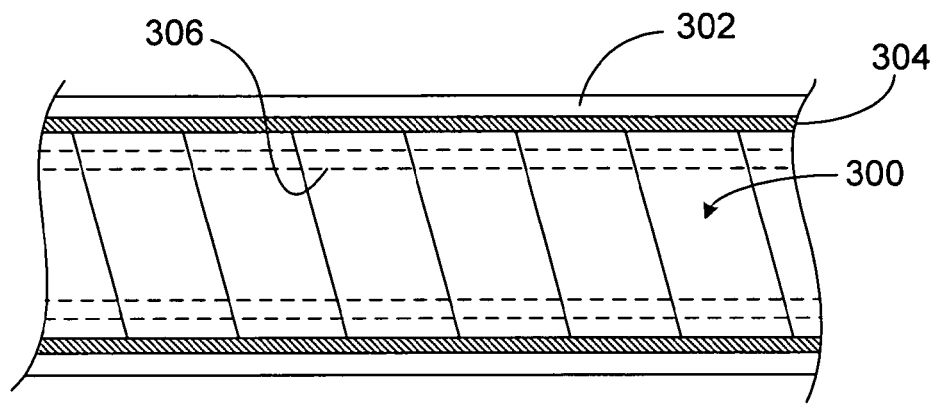
FIG. 7 is a partial side view of an embodiment of a coil of an inner member of an endoprosthesis delivery system.

While embodiments in which a coil is surrounded by a single outer layer have been described, an outer coating may have a plurality of layers. For example, referring to FIG. 7, a coil 300 is surrounded by an outer coating 302 and an intermediate coating 304 disposed between the coil 300 and outer coating 302. Coil 300 surrounds an inner coating 306.

Intermediate coating 304 is generally formed of a material that bonds well to or can be secured well with respect to both coil 300 and outer coating 302. In general, outer coating 302 is more lubricious than intermediate coating 304, which helps secure the outer coating with respect to coil 300. In some embodiments, intermediate coating 304 is an adhesive (e.g., an anhydride-modified polyolefin such as a Plexar). In some embodiments, the outer coating is a polyethylene (e.g., a high density polyethylene or a blend of high and low density polyethylenes). Other suitable materials to form coatings 302 and 304 are described with respect to coatings 62 and 64.

Figure 8:
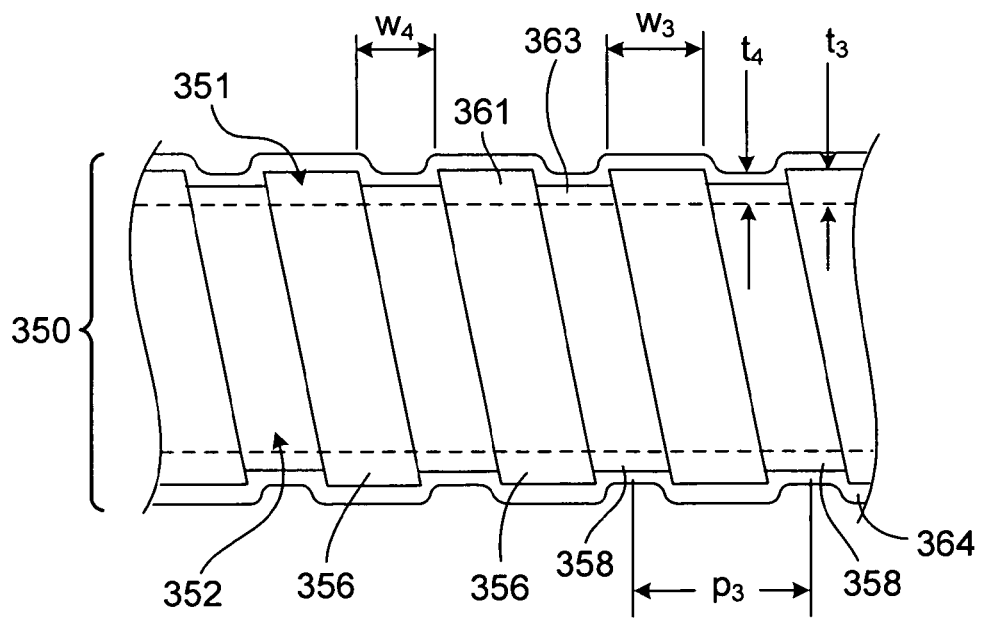
FIG. 8 is a partial side view of an embodiment of a coil of an inner member of an endoprosthesis delivery system.

While embodiments in which a coil is defined by a single filar have been described, a coil may be defined by more than one filar. For example, referring to FIG. 8, a coil 350 of an inner member is defined by a first filar 351 and a second filar 352. Filars 351, 352 are adjacent one another and respectively form adjacent windings 356, 358. A coating 364, which may be the same as other coatings described herein, contacts at least an outer surface of coil 350.

A cross section 361 of filar 351 and a cross section 363 of filar 352 are generally similar (e.g., both are generally polygonal in shape).

Filar 351 has a width w3 and a thickness t3. Filar 352 has a width w4 and a thickness t4. In general, width w3 of filar 351 is larger than width w4 of filar 352. In some embodiments, width w3 is at least about 10% (e.g., at least about 20%, at least about 30%, at least about 50%) larger than width w3.

In general, thickness t3 of filar 351 is larger than thickness t4 of filar 352. In some embodiments, thickness t3 is at least about 10% (e.g., at least about 20%, at least about 30%, at least about 50%) larger than thickness t3.

Figure 9:
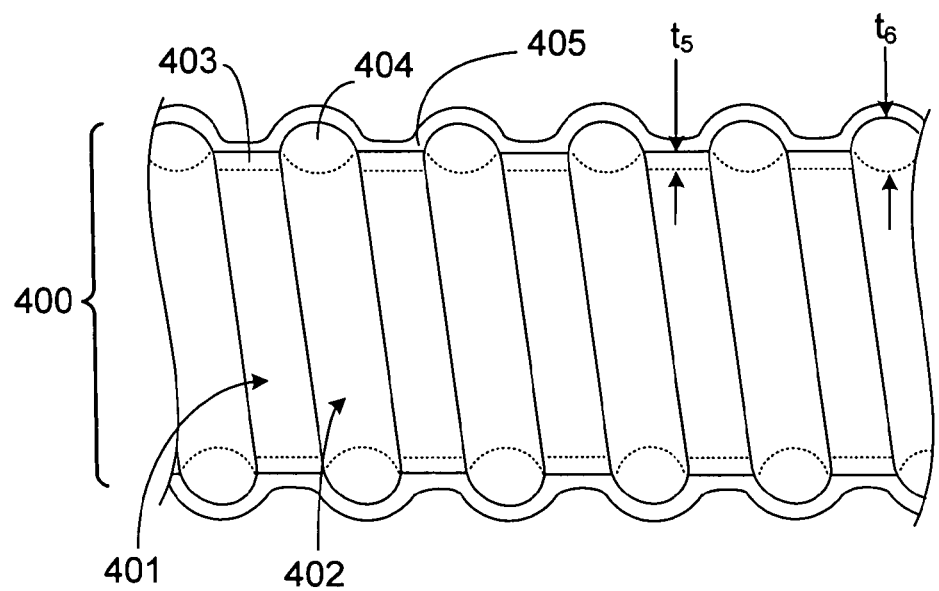
FIG. 9 is a partial side view of an embodiment of a coil of an inner member of an endoprosthesis delivery system.

One or more coils of an inner member can include filars having different cross-sectional shapes. For example, referring to FIG. 9, a coil 400 of an inner member is defined by a first filar 401 having a generally polygonal (e.g., rectangular or square) cross section 403 and a second filar 402 having a generally arcuate (e.g., round or oval) cross section 404. Filar 401 has a thickness t5 and filar 402 has a different thickness t6. Coil 400 is surrounded by a coating 405, which may be the same as other coatings described herein.

Without wishing to be bound by theory, it is believed that a coil with adjacent windings of different cross-sectional shapes (e.g., one polygonal and one arcuate) can exhibit enhanced flexibility and/or a reduced tendency for adjacent windings to undercut (e.g., when moving through lumen 24) as compared to a coil with adjacent windings of similar cross sectional shapes. Coating 405 can further reduce a tendency of adjacent windings to undercut.

While coils defined by generally solid filars have been described, a filar may have other configurations. For example, referring to FIG. 10, a coil 450 is defined by a filar 451 having a plurality of apertures 452, which have a lateral dimension d3 and a longitudinal dimension d4. Filar 451 has a width w5.

Figure 10:
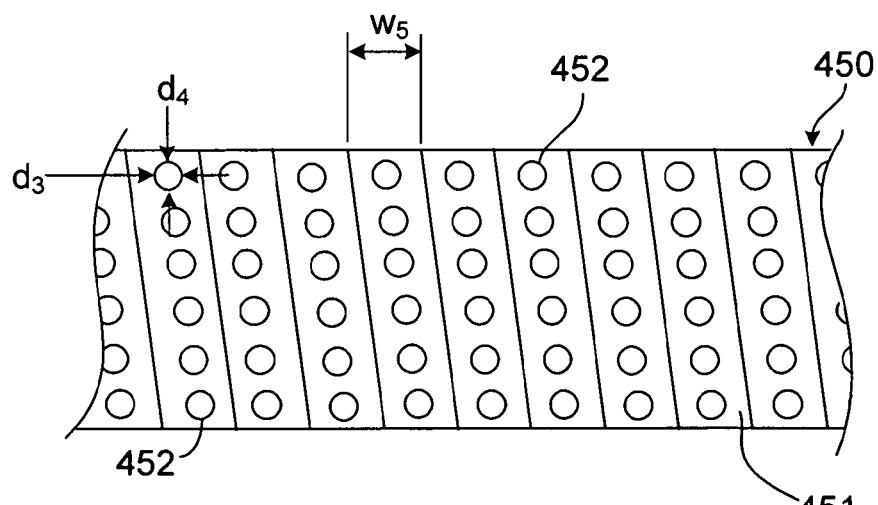
FIG. 10 is a partial side view of an embodiment of a coil of an inner member of an endoprosthesis delivery system.

In some embodiments, lateral dimension d3 of apertures 452 is at least about 20% (e.g., at least about 35%, at least about 50%, at least about 75%) of width w5. As seen in FIG. 10, longitudinal dimension d4 of apertures 452 is the same as lateral dimension d3. In some embodiments, the lateral and longitudinal dimensions of an aperture are different. For example, the longitudinal dimension of an aperture may be elongated or shortened with respect to the lateral dimension.

While coil 450 has been shown with apertures, other configurations are possible. For example, a filar of a coil may have indentations as opposed to or in combination with apertures. Such indentations may extend only a portion (e.g., no more than about 75%, no more than about 50%, no more than about 25%) through the thickness of the filar. The indentations may have lateral and/or longitudinal dimensions as described for apertures 452.

Without wishing to be bound by theory, it is believed that the presence of apertures and/or indentations in one or more filars of a coil can enhance flexibility of the coil while retaining compression resistance.

Apertures and/or indentations of a coil can be formed as desired. For example, apertures and/or indentations can be formed in a filar by laser cutting, mechanical stamping, or chemical etching.

Figure 11A:
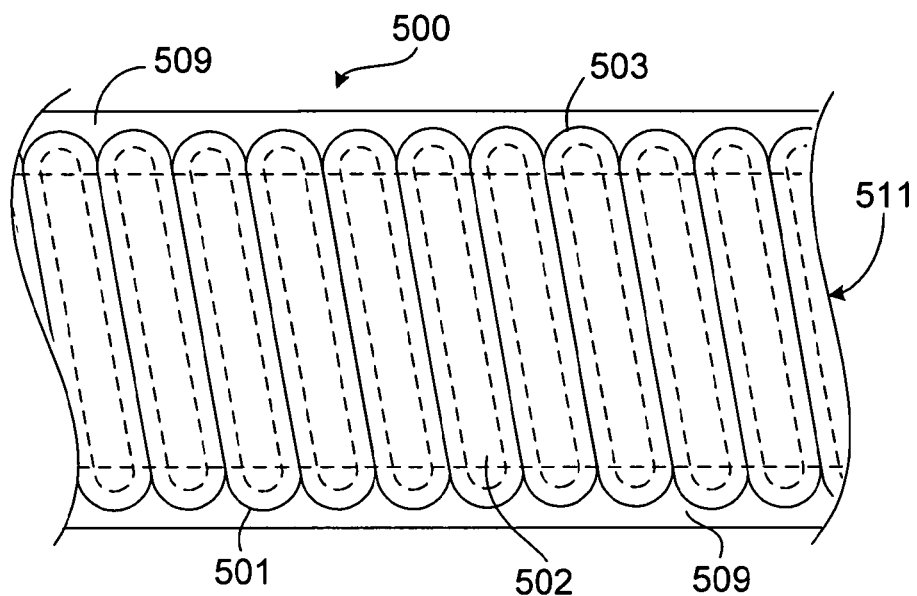
FIG. 11a is a partial side view of an embodiment of an inner member of an endoprosthesis delivery system.
Figure 11B:
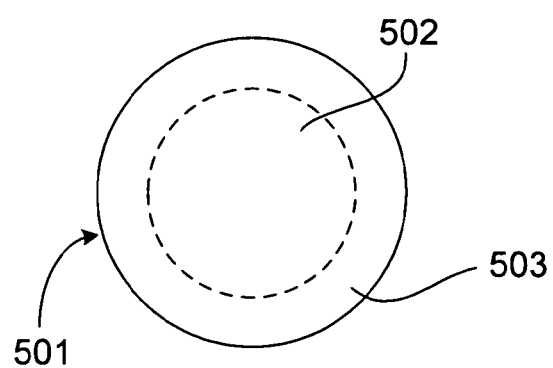

While filars formed of a single material have been described, one or more filars of a coil can be formed from more than one material. For example, referring to FIGS. 11a and 11b, a coil 500 includes a filar 501 having an inner portion 502 that is surrounded by an outer portion 503. An interior of coil 500 defines a guidewire lumen 511. An outer layer 509 surrounds coil 509.

Inner portion 502 of filar 501 can have properties (e.g., outer diameter(s), filar width(s), filar thickness(es), distance(s) between adjacent windings, pitch(es), filar material, filar cross sectional shape(s)) the same as or similar to other filars described herein. Outer portion 503 can be, for example, a polymeric material, such as a plastic (e.g., a thermoplastic), polyamides (e.g., a Nylon such as Nylon 12), polyurethanes, styrenic block copolymers, nylons, thermoplastic polyester elastomers (e.g., Hytrel®), copolyester elastomers (e.g., Arnitel® copolyester elastomers), polyether-block co-polyamide polymers (e.g., PEBAX®) and HDPEs), fluorinated polymers (e.g., PTFE).

Tube 509 is typically made of a polymeric material, such as a material described with respect to tube 54.

In some embodiments, outer portion 503 is integral with the outer surface of tube 509. This can, for example, assist in maintaining the position of coil 500 constant with respect to tube 509.

In an exemplary embodiment, filar 501 includes a metallic inner portion having a generally rectangular (e.g., flat cross section) and an outer portion formed of a lubricious material (e.g., PTFE). Outer portion 509 is formed of a reflowable polymeric material (e.g., a polyamide or a polyether-block co-polyamide polymer).

Coil 500 can be prepared as desired. Typically, the method includes winding filar 501 around a mandrel. The winding can be performed tightly so that adjacent windings are separated by little or no distance such as described for embodiments of proximal coil 50. Tube 509 is positioned around the coil and heated to reflow the material of the tube in contact with windings of coil 500.

Figure 12:
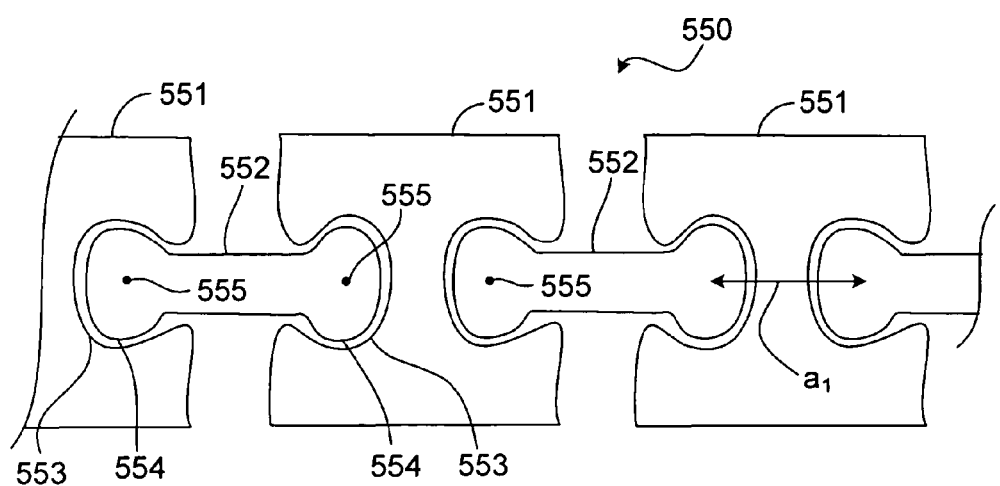
FIG. 12 is a partial side view of an embodiment of a linkage of an inner member of an endoprosthesis delivery system.

While inner members having one or more coils have been described, inner members can have other configurations. For example, referring to FIG. 12, a linkage 550 includes a plurality of first links 551 and a plurality of second links 552.

First links 551 include at least one socket 553 and each second link 552 include at least one projection 554 that is received within a socket of a first link.

Sockets 553 and projections 554 are sized and configured to allow adjacent first and second links 551, 552 to pivot with respect to one another about a pivot point 555 but to reduce (e.g., prevent) linear movement along an axis a1 between adjacent links. For example, sockets 553 and projections 554 can be configured as ball and socket joints. In general, adjacent links 551, 553 have sufficient relative pivoting movement to allow linkage 550 to navigate lumen 24. The amount of linear movement along axis a1 is sufficiently small than linkage 550 resists shortening when subjected to compression (e.g., when outer member 14 is withdrawn proximally to deploy stent 32).

While certain embodiments have been described, other embodiments are possible.

While inner members having a proximal coil and a distal coil with windings of the same orientation, other configurations can be used. For example, in some embodiments, an inner member includes a proximal coil with windings having a first orientation (e.g., clockwise proceeding distally along the coil) and a distal coil with windings having a second orientation (e.g., counterclockwise proceeding distally along the coil) opposite to the first orientation.

While inner members with coils having one or two filars have been described, coils may have more filars. For example, one or more coils of an inner member can have at least 3 filars (e.g., 4 filars, 5 filars, or more). In embodiments where a coil has more than one filar, the filars may have the same or different geometries and/or sizes. For example, the cross-section shapes, widths, and/or thickness of at least some (e.g., all) filars of a coil may be the same or different. A proximal coil of an inner member can include one or more filars that is common with a distal coil of the inner member and one or more filars that is not common to the distal coil.

While inner members with coils having a filar that is wider than it is thick have been described, filars can have other geometries. For example, one or more filars of a coil can be at least as thick as wide. In some embodiments, a ratio of a filar's thickness to its width is greater than 1 (e.g., at least about 1.1, at least about 1.2, at least about 1.3). At least one filar of a coil can have a greater thickness and a smaller width than another filar of the coil.

While inner members with coils having one or more filars with generally uniform shapes along their lengths have been described, other configurations may be used. For example, one or more filars of a coil may have a thickness and/or width that increases proceeding, for example, proximally along the coil. As another example, a number and/or size of apertures and/or indentations may increase proceeding, for example, distally along a coil.

While inner members that have a distal coil with a proximal end disposed generally adjacent to a distal end of a proximal coil have been described, the coils can have other configurations. For example, a distal coil can extend proximally within at least a portion (e.g., most or all) of a proximal coil. The inner diameter of the proximal coil is typically as large as or larger than the outer diameter of the distal coil. In such embodiments, the interior of the distal coil can define a guidewire lumen along at least a portion (e.g., most or all) of the length of the inner member.

Other embodiments are within the scope of the following claims.

What is claimed is:

1. An implantable medical endoprosthesis delivery system, comprising:
    an outer member; and
    an inner tubular member disposed within the outer member, the inner tubular member defining a guidewire lumen and having a distal tip with a distal opening in fluid communication with the guidewire lumen, the inner tubular member comprising a coil having a proximal coil portion and a distal coil portion, the distal coil portion including windings having a spacing therebetween that differs from a spacing, if any, between windings of the proximal coil portion,
    wherein:
        the spacing between the windings of the distal coil portion is greater than the spacing, if any, between windings of the proximal coil portion;
        at least some of the windings of the distal coil portion surround the guidewire lumen of the system;
        the windings of the distal coil portion have an outer diameter that is smaller than an outer diameter of the windings of the proximal coil portion; and
        an implantable medical endoprosthesis is disposed radially between the outer member and the windings of the distal coil portion.

2. The implantable medical endoprosthesis delivery system of claim 1, wherein an average distance between adjacent windings of the distal coil portion is at least about 20% of an average width of the windings of the distal coil portion.

3. The implantable medical endoprosthesis delivery system of claim 2, wherein the average distance between adjacent windings of the distal coil portion is at least about 30% of the average width of the windings of the distal coil portion.

4. The implantable medical endoprosthesis delivery system of claim 1, wherein the proximal coil is defined by a plurality of windings and an average distance between adjacent windings of the distal coil is at least about 2 times greater than an average distance between adjacent windings of the proximal coil.

5. The implantable medical endoprosthesis delivery system of claim 4, wherein the average distance between adjacent windings of the distal coil is at least about 10 times greater than the average distance between adjacent windings of the proximal coil.

6. The implantable medical endoprosthesis delivery system of claim 1, further comprising a polymeric coating that contacts an outer surface of the coil.

7. The implantable medical endoprosthesis delivery system of claim 6, further comprising a tube at least partially surrounded by the coil, wherein the polymeric coating secures at least some of the windings of the distal coil portion with respect to the tube.

8. The implantable medical endoprosthesis delivery system of claim 6, wherein the polymeric coating is formed from a material having a durometer of about 50 D or less.

9. An implantable medical endoprosthesis delivery system, comprising:
    an outer member; and
    an inner member disposed within the outer member, the inner member comprising a coil having a proximal coil portion and a distal coil portion, the distal coil portion including a plurality of windings spaced apart a distance different than a distance, if any, spacing apart windings of the proximal coil portion,
    wherein:
        wherein the spacing between the windings of the distal coil portion is greater than the spacing, if any, between winding of the proximal coil portion;
        the windings of the distal coil portion have an outer diameter that is smaller than an outer diameter of the windings of the proximal coil portion;
        at least some of the windings of the distal coil portion surround a tube at least partially defining a guidewire lumen of the system; and an implantable medical endoprosthesis is disposed radially between the outer member and the windings of the distal coil portion.

* * * * *